United States Patent [19]

Novini

[11] Patent Number: 5,095,204
[45] Date of Patent: Mar. 10, 1992

[54] MACHINE VISION INSPECTION SYSTEM AND METHOD FOR TRANSPARENT CONTAINERS

[75] Inventor: Amir R. Novini, Akron, Ohio
[73] Assignee: Ball Corporation, Muncie, Ind.
[21] Appl. No.: 575,162
[22] Filed: Aug. 30, 1990
[51] Int. Cl.[5] ............................................. G01N 9/04
[52] U.S. Cl. ................................. 250/223 B; 356/240
[58] Field of Search ..................... 250/223 B; 356/239, 356/240; 209/524, 526, 528

[56] References Cited

U.S. PATENT DOCUMENTS

| | | | |
|---|---|---|---|
| 3,245,533 | 4/1966 | Rottmann | 209/111.7 |
| 3,533,704 | 10/1970 | Krenmayr | 356/198 |
| 3,687,559 | 8/1972 | Fischer | 356/240 |
| 4,025,202 | 5/1977 | Deane | 356/240 |
| 4,249,075 | 2/1981 | Lovalenti | 250/223 B |
| 4,428,673 | 1/1984 | Yoshida | 250/223 B |
| 4,476,533 | 10/1984 | Daudt et al. | 364/473 |
| 4,606,634 | 8/1986 | Bieringer | 356/240 |
| 4,831,250 | 5/1989 | Fukuchi et al. | 250/223 B |
| 4,861,164 | 8/1989 | West | 356/445 |
| 4,899,295 | 2/1990 | Nonweiler | 364/522 |
| 4,900,916 | 2/1990 | Cormack | 250/223 B |

Primary Examiner—David C. Nelms
Assistant Examiner—Khaled Shami
Attorney, Agent, or Firm—Gilbert E. Alberding

[57] ABSTRACT

A system and method for optical inspection of the bottom surfaces of transparent containers comprises an image acquiring means, an illumination source and means for processing, storing and analyzing the image to search for and identify a baffle mark in the acquired image, and when found, to remove or erase the baffle mark from the image memory prior to the defect inspection process. Significant defects present in the area of the image being searched can be identified, even if the defects are located directly on the baffle mark, thus providing high sensitivity capabilities for defect detection while maintaining a low false rejection rate due to baffle marks.

47 Claims, 9 Drawing Sheets

FIG. 1
PRIOR ART
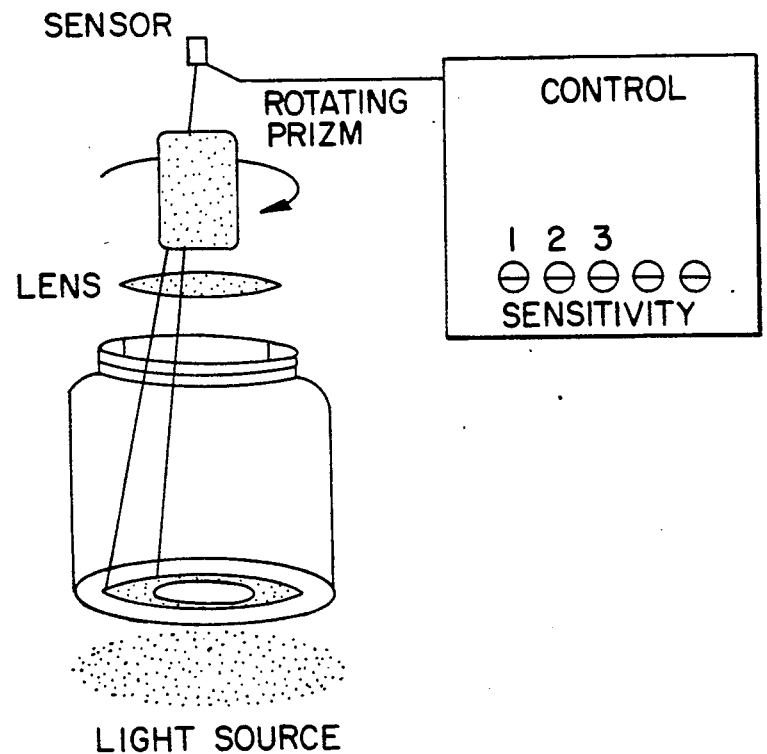
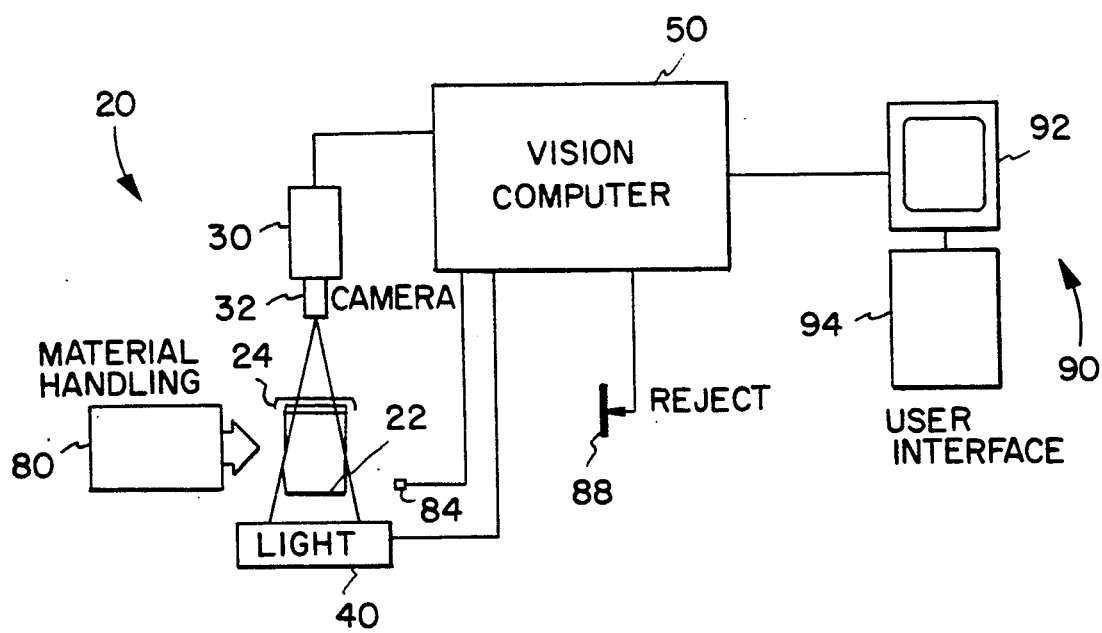
FIG. 2

FIG. 7A
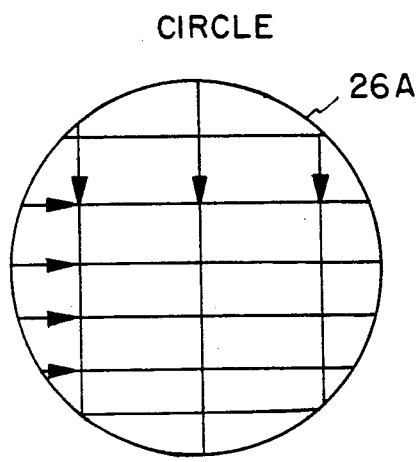
FIG. 7B
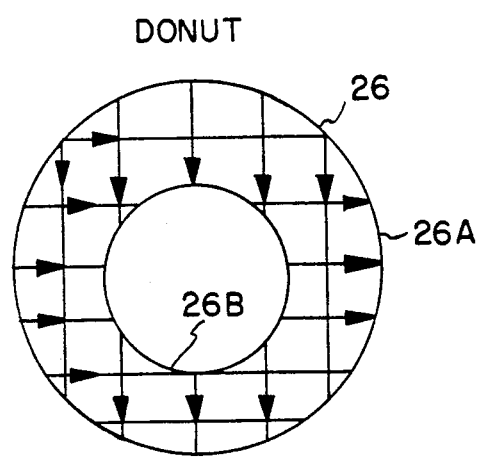
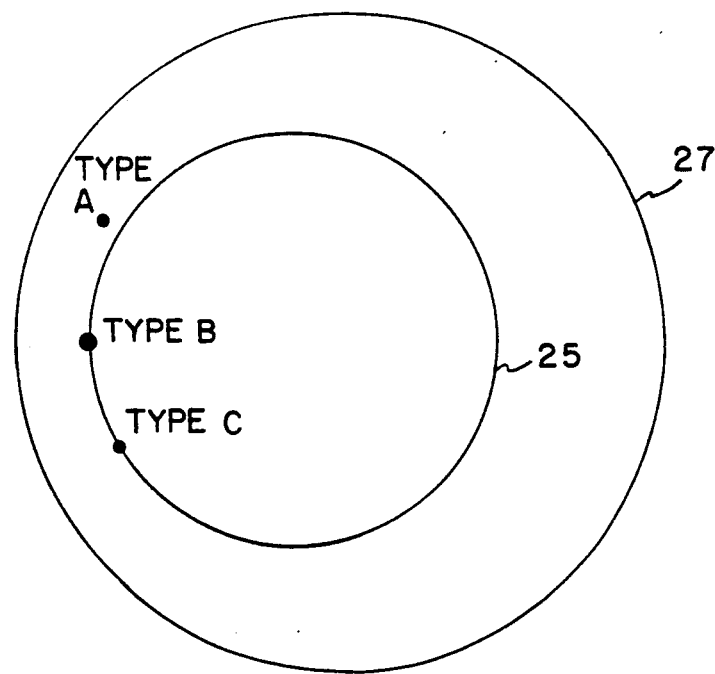
FIG. 8

MACHINE VISION INSPECTION SYSTEM AND METHOD FOR TRANSPARENT CONTAINERS

TECHNICAL FIELD

This invention relates to non-contact means for inspecting containers, and more particularly relates to a machine vision system for detecting imperfections formed in the bottom surface of transparent containers having baffle marks formed therein.

BACKGROUND ART

A typical glassware manufacturing plant includes a forming machine, also known in the trade as an individual section or IS machine, and a "gob feeder" mechanism. A forming machine typically includes 6-10 identical individual sections for producing finished glassware such as bottles or jars. The gob feeder mechanism feeds a gob of molten glass to each of the sections of the forming machine in turn. As an article of glassware issues from each of the sections, it is carried by a conveyor through an inspection area where the glassware is inspected for flaws. The flaw inspection is normally accomplished by either the actual observation of a human being stationed at the inspection area or by a video camera inspection system.

Three areas of a glass container are generally inspected for flaws. The top and thread area is inspected for defects on the seal surface and for thread flaws. The sidewall of the container is inspected for defects in the glass container walls such as cracks, bubbles, bird-swings, etc. The bottom surface area of the container is inspected for a long list of flaws that include, among others, loose and fused glass, spikes, bird-swings, stones and bubbles, and mold dope.

Most glassware is manufactured to bear some indication of its origin by placement of certain mold markings on the outside base of the container. These markings may take the form of letters, numbers, or abstract designs. The presence of the various types of markings plus the fact that the same markings do not always appear in the same physical location has made automatic inspection of glass bottoms inherently difficult.

Moreover, most troublesome is the "baffle mark" formed in the bottom surface of a glass container. The baffle mark is a mold marking which is a by-product of the two-step glass manufacturing process and is generally circular in shape and may appear in different locations on the bottom of the container. It is generally an acceptable (by glass manufacturer and user) condition. In the automatic inspection of glassware by optical systems, the baffle mark can produce a high contrast signal which is often confused with the signal from a defect, thereby resulting in the rejection of acceptable glassware.

A defect in the glass represents an optical boundary layer which reflects or refracts an incident light beam producing a light contrast which can be detected optically. The great disadvantage of known optical test arrangements of this type consists in that they cannot distinguish between actual defects and other optically effective faults in the test element. For example, there are many types of faults, such as small included air bubbles, relatively small ribs or seams, etc., which do not have any deleterious effect on glassware, but which act similarly to a defect in optical test arrangements so that acceptable glassware is rejected. Because of the inability to distinguish between unacceptable defects and faults that can be tolerated, prior systems have been prone to accept defective glassware or, with more sensitive settings, to reject acceptable glassware.

Further, in detecting defects in glass articles, the articles have usually been illuminated with a diffused backlight, and viewed with a television camera or light sensitive sensor array. The light source often consists of a plurality of incandescent bulbs that produce generally a relatively large diffused source for backlighting the container at the inspection station or zone. A linear array television camera, focused on a portion of the container to be inspected, will provide an image of that portion onto the array of picture elements (commonly referred to as "pixels") in the camera. The pixels then are serially interrogated and the outputs of the pixels, which is a function of the intensity of the light received thereon, are compared. Defects in the container portion being inspected can be detected by analysis of the pixel outputs of the linear array.

In such systems, when a defect appears in the container as that portion is moved through the field of view area of the camera, the pixels upon which the portion is being focused will see areas of darkness caused by the reflection of the illuminated light out of the line of sight of the pickup. In this way, by comparing the output of adjacent pixels one can determine where the defect lies and the size of the defect. The pixels may be scanned at a sufficient rate so that essentially every area of the bottle is viewed. Most defects actually will span more than a single scan and will appear in several successive scans.

It has further been the practice to optically detect defects in glassware in various portions of a glass article by focusing a beam of light onto an area of the article at a particular angle and then positioning a pickup, such as a photocell, at approximately a 90° angle with respect to the direction of the focused light. In such an arrangement, the light will be reflected from the defect onto the photocell, thus indicating the presence of a reflective defect. This has been the typical practice for examining the finish and heel portions of glass containers in the past. Defects which are being detected by such systems are those typically termed "checks", caused usually by thermal shocks during the formation of the container from the touching of the hot formed glass to a cold piece of handling equipment. Another defect which can be picked up by the use of specular, focused light are surface defects produced in glass containers which will cause the focused light to be refracted out of the direction in which it is being transmitted to the container, for example, a line-over-finish defect.

Another means by which glassware may be inspected is a machine vision system. Machine vision is the technology of acquiring or sensing an image (a visual impression) of a selected portion of the glassware through an electronic sensor and determining the existence of any marks or defects in the image and the acceptability of any such marks or defects by use of a computer. The technology is based around a television camera to acquire the image and dedicated vision computers to process and analyze the images from components/products with speed and repeatability. While human vision may outperform its automatic equivalent in its sheer ability to analyze very complex, every-day scenes; when it comes to repeated tasks, such as inspection of a product over and over again, a human observer understandably tires, loses concentration, and makes mistakes.

Machine vision can also be more cost-effective and sometimes the only viable solution if speed and/or hazardous conditions are present in the manufacturing process. The possible uses of machine vision technology include assembly/process verification, gauging, character verification and recognition, surface flaw detection, sorting systems, and robotic guidance. In many of these applications, machine vision systems can also provide important and accurate process control information since 100 percent of the product can generally be examined. This information can help identify the "problem area(s)" of the process so it can be corrected to reduce scrap and improve quality.

As noted above, automatic electro-optical inspection of glassware is well known; however, machine vision inspection methods of glass containers have developed only recently. A significant distinction between the two methods of inspection is the manner by which each system captures the image of the object being inspected and then analyzes that image to form an opinion on its status, i.e., acceptability.

Electro-optical scanning for glass bottom inspection has provided the glass manufacturer and the end user (prior to filling operations) with automatic inspection of their product for years. One such conventional system is shown in FIG. 1 wherein the system utilizes a diffused back light with an incandescent source. The empty glass container travels through the optical path by the dedicated material handling system (a star-wheel mechanism, for example). While the jar is in the optical path, it is scanned by a rotating prism which projects a revolving image of the bottom of the container through a lens onto a series of photosensors. Each sensor then scans a circular band area with all the sensors in combination providing complete coverage of the jar bottom. The signals from the sensors are fed into electronic discrimination circuits which analyze the incoming signal for changes/absolute values in the light level for defect detection.

The system is simple in principal and operation but requires precision part placement. This normally is achieved by some form of star-wheel mechanism that requires changeover parts to adapt the system for inspection of different container sizes/shapes. Poor repeatability in sensitivity setup, inability to examine non-round containers, and high false reject rates with the high sensitivity settings are among the shortcomings of such prior electro-optical scanning systems.

Machine vision inspection of glass containers offers some worthwhile advantages over the more established electro-optical scanning methods. These include sophisticated image processing/analysis, highly repeatable setup and performance, TV camera image available for easy diagnosis and setup, ability to inspect non-round containers, less precision in required part placement, and easier change over for other container shapes/sizes.

The basic components of a machine vision system include a material handling system, a lighting system, image acquiring means and image processing means. The material handling system manipulates and presents the part to the machine vision imaging system and generally includes the part sensing (photo-eye, proximity switch, etc.) and a defect removal mechanism. Machine vision systems can be either adapted to an existing material handling system, or a specific material handling system can be designed for the parts to be inspected.

The lighting system of a machine vision system illuminates the parts to be inspected. High contrast between the feature of interest (e.g., a defect) and its background (the non-defective area surrounding the defect) is desirable. The lighting system should also reduce the effects of unwanted feature information and provide the user with a stable, long-lasting and environmentally safe light source for inspection.

Two important aspects of a lighting system include the lighting technique and the light source. The lighting technique refers to the physical arrangement of the light source in relation to the part under inspection and the television camera. The lighting technique in its most fundamental concept is divided into front lighting and back lighting. Either can be accomplished with the use of structured or unstructured light.

Front lighting refers to the technique where the light source and the television camera are on the same side of the part being inspected. The angles and distances between the light source, part and camera are important and will determine the contrast of the image. Front lighting is generally used to view and extract surface features of objects.

Back lighting refers to lighting systems in which the light source and the television camera are on opposite sides of the object being inspected. This technique produces a high contrast silhouette image of an optically opaque object. With transparent objects such as glass containers, the contrast is produced by features changing light transmission, and/or light reflection, and/or light refraction.

The general list of illumination sources for machine vision include incandescent lamps, fluorescent lamps, xenon flash tubes, light emitting diodes, lasers and x-rays. For packaging or manufacturing applications, generally a strobe light is needed since the inspection is performed on moving objects. Two common strobe lights are the xenon flash tubes and light emitting diodes.

A light emitting diode (LED) is a solid state device which emits light when forward biased. The LEDs can be turned on and off quickly; therefore, they can act as a strobe light in a similar manner to the xenon flash. Generally, several LEDs form a strobe light with a single trigger and drive circuit to produce adequate light to illuminate an object. The LEDs are generally driven with current pulses much higher than the normal continuous operation currents to produce a short, but bright, pulse of light.

The optical components of a machine vision system normally include a lens that is attached to the image acquiring means defined by a television camera. Through this lens, an image of the object to be inspected is formed. The focal length of this lens and standoff distance (distance between the object and the lens) will determine the field of view. The field of view is preferably kept to a minimum to provide the system with the most accurate image interpretation and yet allow for normal part position variation. Two basic types of lenses include fixed focal length and variable focal length or zoom lens.

Other optical components include mirrors, beam splitters (partially silvered mirrors that can reflect and transmit light at the same time), color filters, polarizers, etc. These additional components are used to either enhance contrast and/or reduce the effect of unwanted information, or obtain the needed optical geometric arrangement in a limited space.

The most common image acquiring or sensing means used with machine vision applications is the solid state CCD- (charge coupled device) or MOS- (metal oxide semiconductor) type black and white television camera. The light sensor in these cameras is constructed of hundreds of thousands of individual solid state light sensitive elements (pixels) which are arranged in a matrix.

The high speed inspection of packaging lines require additional features that are generally not available on most cameras. One such feature has to do with the asynchronous timing relationship between the part's arrival at the inspection area in front of the camera and the camera's internal timing sequences. The typical part velocity is such that no delay between part arrival and picture acquisition can be tolerated; therefore, the camera's timing signals must be interrupted to allow it to acquire an image of the object immediately. This feature is sometimes referred to as "frame reset" capability and is only available on cameras designed for machine vision or similar scientific applications.

There are many different vision processors commercially available today for use with machine vision systems to process and analyze the image once acquired. Some are designed for specific tasks while some are meant as general purpose platforms. Most systems, however, will acquire and store a two-dimensional image from the television camera and then process and analyze the image by some form of computer. There are also many variations on the image processing and analysis algorithms. Often the machine vision hardware is designed for efficient implementation of those algorithms to achieve the high product throughput of packaging and pharmaceutical lines.

Three different basic arrangements of machine vision hardware are common and these are: dedicated hardware processors; parallel processors; and multiple processors.

Dedicated hardware processors are types of machine vision hardware in which the image processing/analysis algorithms are either partially or fully implemented in electronics hardware. This type of approach makes sophisticated high speed (greater than 2000 ppm) inspection possible. However, since the inspection algorithms are generally fixed in hardware, they are difficult to change for further enhancement and/or adoption to a new task.

The parallel processor technique relies on multiple processing networks that operate on the same image. This type of approach can provide high speed and sophisticated inspection techniques and maintain some flexibility in algorithm approach.

The multiple processor approach utilizes multiple complete-image acquire and process channels that share the incoming images from the television camera to speed up the system throughput. By increasing the number of processing channels, the higher throughput speeds are achieved. This type of multiprocessor software-based approach offers flexibility in algorithm selection and processing for high speed applications.

A major shortcoming in the application of conventional machine vision systems to the inspection of conventionally made glassware is their inability to deal with the baffle marks formed in the bottom surface of a glass container. Thus, there has developed a need for a means and method of inspecting the bottom surface of a glass container having a baffle mark formed therein to distinguish the acceptable baffle mark from unacceptable defects present in the bottom surface to effect the removal of unacceptable containers from the manufacturing system.

SUMMARY OF THE INVENTION

This invention presents a system and method for inspecting the bottom surface of transparent containers employing an image acquiring means, an illumination source and means for processing, storing and analyzing the image to search for and identify the baffle mark in the acquired image, and when found, to remove or erase the baffle mark from the image memory prior to the defect inspection process. The system and method of the invention can identify significant defects present in the area of the image being searched, even if the defect is located directly on the baffle mark. The invention can thus provide high sensitivity capabilities for defect detection while maintaining a low false rejection rate due to the baffle mark.

This invention generally comprises an illumination source comprising a solid state strobe lighting system, image acquiring means comprising a television camera equipped with a lens to acquire an image of the bottom surface, means for processing and analyzing the bottom surface image comprising a microprocessor, and interface means to permit variable programming of the system microprocessor for desired inspection tasks through a user-interaction system of menus. The system of this invention is preferably combined with a material handling system which transports and presents the glass container to the machine vision system invention.

The system of this invention is operable in two modes: a training mode and an inspection mode. Prior to the initiating of any inspection sequence, the system is first operated in the training mode to provide the system with criteria for acceptable glass containers (containers that previously have been determined as acceptable by whatever means). In the training mode, an acceptable container is placed in the field of view of the image acquiring means to permit the system to acquire the image of the bottom surface of the acceptable container. The operator then defines a set of acceptable parameters for this image, including a pass/fail sensitivity factor. This "good" or acceptable container information is then stored in the storage means. The system is then ready to operate in the inspection mode.

While in the inspection mode and during the inspection sequence, the system acquires the image of the bottom surface of each container, identifies the baffle mark within the image and erases or removes it from the image memory, inspects the remaining image by analyzing and processing any marks or defects discovered in the image and compares these findings to the predetermined acceptable parameters to determine whether the container is acceptable, and generates a rejection signal if the container is unacceptable. The system conducts an objective pass or fail inquiry to either a pass or fail to each container depending on the test comparisons. The rejection signal can be used to remove unacceptable containers at the inspection station or can be directed to remote machinery to effect the removal of bad or unacceptable containers.

This invention also provides a method by which the quality and acceptability of glass containers may be quickly and accurately determined. The method is carried out as described above by sensing the presence of a container at the inspection zone, illuminating the bottom surface of the container and acquiring its image, identifying the baffle mark present in the image and erasing the baffle mark from the image memory, inspecting the remaining image, comparing any marks or defects found in the image with criteria of acceptability and determining whether such marks or defects are acceptable, and effecting the removal of the container if any such marks or defects are unacceptable.

Further features of the invention will be apparent from the following drawings and disclosure of preferred embodiments of the invention and their method of operation.

BRIEF DESCRIPTION OF THE DRAWINGS

FIG. 1 is a partial perspective and schematic view of a prior art electro-optical scanning method for inspecting the bottom surface of glass containers;

FIG. 2 is a schematic view of a machine vision system provided by this invention;

FIGS. 3 and 3B are a schematic view of an image acquiring means incorporated by the machine vision system of FIG. 2 illustrating a diffused light source employed by this invention;

FIGS. 5A and 5B are plan views of an image of the bottom surface of a container being inspected by the the invention to illustrate the manner by which the invention identifies the baffle mark and removes it from the image memory of the invention;

FIGS. 7A and 7B are plan views of an image of the bottom surface of a container being inspected by the invention to illustrate the manner by which the invention processes the image utilizing a linear edge detection method to detect defects or otherwise unacceptable marks in the bottom surface;

FIG. 8 is a plan view of the bottom of a glass container to illustrate the ability of the invention to detect defects in the presence of a baffle mark.

BEST MODE FOR CARRYING OUT THE INVENTION

Figure 3:
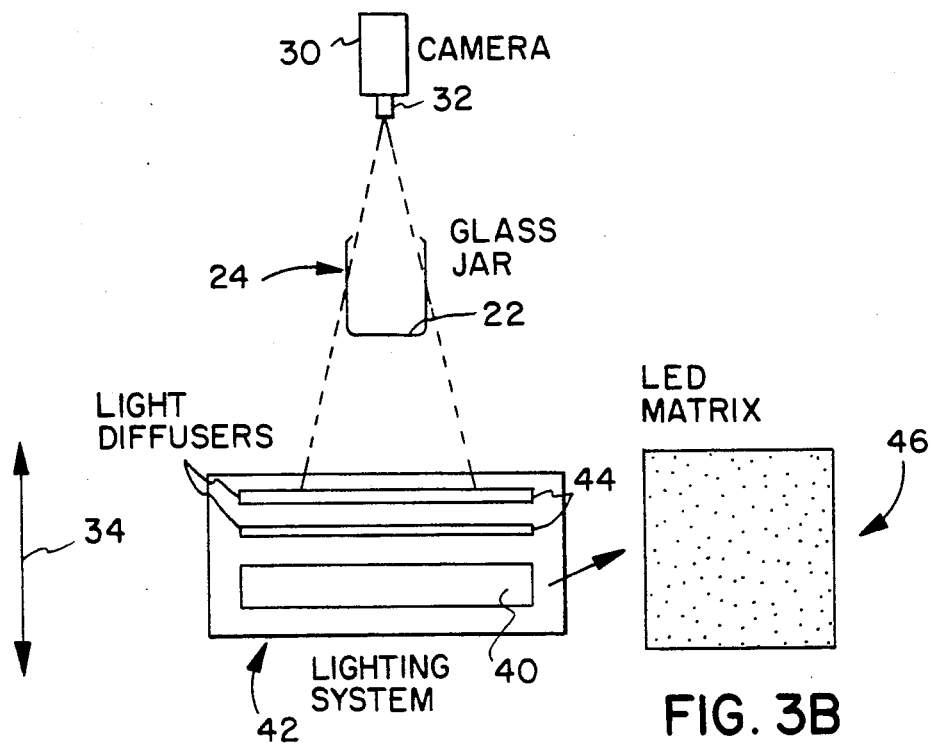
Figure 4:
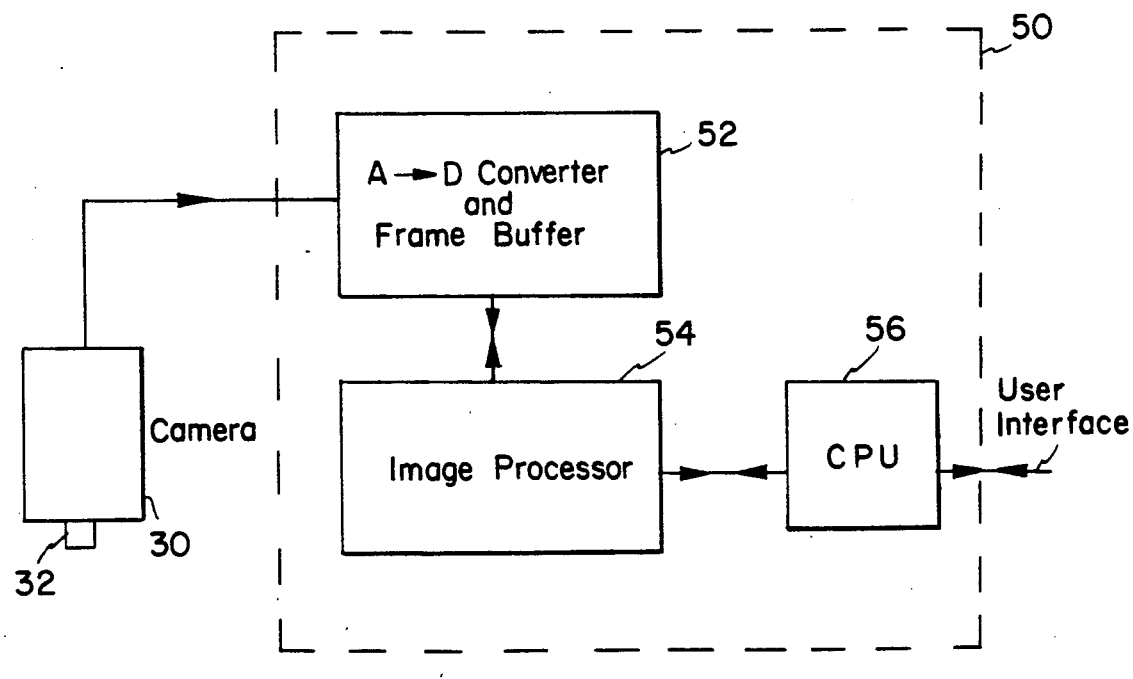
FIG. 4 is a block diagram of a simple inspection system of FIG. 2.

A system 20 presented by this invention is illustrated in FIGS. 2-4 wherein like reference numerals correspond to like components. A preferred method by which this invention acquires, inspects and analyzes the image of the bottom surface of a container is illustrated in FIGS. 5A-8. A preferred method of inspecting the bottom surface of transparent containers presented by this invention is shown by flowcharts in FIGS. 9-12B.

Referring now to FIGS. 2-4, the system 20 of this invention may be broken down for better understanding into generally four major components: (1) a front end means for acquiring the image of the bottom surface of the container for inspection and analysis; (2) a vision engine means for analyzing the image information and making decisions; (3) operator interface means for communicating between the operator and the system 20; and (4) machine interface means for communicating between the system 20 and the controls of other machinery.

The front end means is an important part of the system 20 because a quality image must first be achieved before any accurate analysis is possible. The front end means of this invention generally includes a lighting system 42, including an illumination source 40 and diffusers 44, a camera 30 and lens 32. This system 20 utilizes a backlighting technique in which the container 24 is positioned between the camera 30 and the lighting system 42 to provide a high-contrast image of the bottom surface. Structural defects in the bottom surface 22 of the container may then easily be detected by system 20. Such defects include foreign objects, cracks, bubbles and holes, and improper dimensions.

Means 50 comprises a computer means for identifying a baffle mark in the acquired image of the bottom surface and erasing the baffle mark from the acquired image prior to the initiation of the inspection sequence.

System 20 further includes a part-present optical sensor 84 and a reject mechanism 88. Part-present sensor 84 is a photoelectric detector which detects the presence of the jar 24 in the inspection area and sends a corresponding part-present signal to the computer means 50 to initiate the image acquiring sequence. Reject mechanism 88 is preferably arranged adjacent the conveyor of the material handling means 80 and is coupled to the vision computer 50 to receive rejection signals from the computer and remove defective or unacceptable containers from the conveyor. Reject mechanism 88 may be provided by various pneumatically actuated reject devices.

System 20 further preferably includes a user interface 90 to provide for programming of the system 20 by the use of a monitor 92, menus presented thereon, and a keyboard 94.

Glassware 24 inspected by this system is examined in a backlighting arrangement where the container 24 is positioned between the illumination source 40 and the image acquiring means 30 to produce an image of the bottom surface 22 of the container. As shown in FIG. 3, illumination source 40 is an integral component of an overall lighting system 42 which includes light diffusers 44 which provide highly uniform illumination of the bottom surface of the container. Light source 40 is preferably constructed of several hundred light-emitting diodes (LEDs) arranged in a matrix 46 as shown in FIG. 3B. LED matrix 46 is triggered by the vision computer 50 when the presence of the glass container 24 in the inspection area is detected by sensor 84. The light output of source 40 is a short pulse (100–600 microseconds) of light which "freezes" the motion of the part with respect to the image acquiring means 30. The solid state LED strobe light 40 provides a highly stable, rugged, and long-lasting strobe light source that is superior to gas-discharged strobes. The enclosure housing the lighting system 42 is preferably designed to swing out from under the system 20 for easy cleaning of the light diffusing surface. If desired, strobes may be sequenced so the glassware can be "imaged" with more than one strobe without the illumination from one test affecting or interfering with other tests. Also, illumination source 40 can provide extra light intensity and, if desired, may be used to enhance a specific part of a light spectrum.

System 20 is preferably used in combination with material handling means 80 to present the container 24 to the inspection area and carry it therefrom to a rejection area. Material handling means 80 is preferably provided by a side-grip conveyor mechanism (not shown) which allows a clear view of the bottom surface of the container. Product change-over is accomplished by incorporating three mechanisms where one mechanism which adjusts the width of a conveyor employed by the handling means, a second mechanism which adjusts vertically the camera's position, and a third mechanism which adjusts vertically the positions of the illumination source. These mechanisms may be made and used by one of ordinary skill and are not described in detail herein. The system of this invention may be adapted to an existing material handling means employed in a manufacturing line, or alternatively, a specific material handling system may be designed for presenting the containers to the inspection system of this invention.

Image acquiring means 30 comprises a television camera equipped with a lens 32. The lens is preferably a fixed focal length type and the television camera is preferably a high resolution, solid state, MOS (metal oxide semiconductor) type with asynchronous frame reset capability. This capability allows the camera 30 to capture the image of the moving container 24 with positional precision. A changeover for other sizes/shapes of containers may be accommodated by simply adjusting the relative vertical positions of the camera 30 and/or the lighting system 42, as generally indicated by reference arrow 34.

An image of the bottom surface 22 of the container is focused into the camera 30 through the optical lens 32. One preferred camera includes a 320 horizontal by 240 vertical sensor cell matrix. Each individual cell of the matrix consists of a separate picture element or "pixel". Each of these 76,800 cells receives a portion of the image and produces an analog voltage from zero to 1V p-p dependent upon how bright the area is. This analog information is then read by a raster scan and sent out as a series of RS170 amplitude modulated pulses to a video multiplexor provided in the image processor 54. During operation, continuous live images from the cameras are passed through the camera distribution board to the image processor board 54 where the images wait to be selected. When a vision inspection sequence is started, the I/O processor housed in CPU 56 signals the image processor 54 which then checks to see if the strobe lighting system 42 has been activated. If not, the image processor instructs the video multiplexor to direct an image from the camera to the converter-frame buffer means 52 for digitization.

The preferred camera 30 of this invention displays virtually no geometric distortion, no image drift, virtually no image lag or image burn. Such a camera is manufactured by Panasonic Corporation as model GP-MF702/Industrial MOS B/W camera. If desired, filters may be placed in front of the lens 32 of the camera 30 or in front of light source 40 to block or pass specific light wave lengths. These additional filters may be used to improve the contrast of the image or enable the system 20 to detect particular colors. Common filters which may be used in the system of this invention are ultraviolet, infrared, red, blue, green and polarizing.

The computer means 50 provided by this invention is preferably based upon a multiprocessor system design as shown in FIG. 4. This multiprocessor system comprises a means 52 for digitizing the analog signals received from the camera 30 to provide an image of the bottom surface and for storing the digitized image in converter-frame buffer means 52. CPU 56 comprises an input-output (I/O) register and housekeeping processor 58 which tracks the position of the individual containers and their test results and provides pass and fail outputs based on the test results to effect the removal of unacceptable containers. Synchronization of the system 20 is provided by vertical and horizontal drive signals generated by the image processor 54 which sends the drive signals to an internal sync board which amplifies the drive signals and passes them through a camera distribution board (not shown) in a standard RS170 format. The camera distribution board contains BNC connectors to distribute the synchronization signals to the camera (into each of the cameras if more than one is used).

The conversion process of the analog image signals generated by camera 30 is carried out by an analog-digital converter housed in means 52 which samples the voltage level of the RS170 signals. A - digital value of one to 256 is then assigned to the signal from each pixel, according to the voltage level which corresponds to the intensity of the illumination of that particular pixel. For example, a black pixel, indicated by very low voltage, is assigned a digital value of one, whereas a white pixel, indicating by a very high voltage, is assigned a digital value of 256. Each pixel is thus assigned a digital value of between one and 256 relative to its intensity. The digitized image is then passed through a look-up table (LUT) before it is stored in the frame buffer 52.

Thus far, the digitized image has been passed through the LUT and stored in the frame buffer 52. To display a stored image on the monitor 92, a second multiplexer chooses to display one of the images stored in the frame buffer means or the live image. The chosen image is then reconverted into an analog signal by a D/A converter connected with the CPU 56 and directed to the monitor 92. The overall resolution of the digitized image is determined by the sensor matrix of camera 30, the A/D converter and the density of the frame buffer. As noted above, the resolution of a preferred system 20 of the present invention is a 320 horizontal by 240 vertical pixel matrix.

As described above, when an inspection sequence is initiated, the analog video signal from the camera 30 is digitized and stored in one of the frame buffers 52. The image is then ready to be analyzed by the image processor 54. The instructions for these processing operations are stored in a PROM and may be communicated to the system 20 through the user interface 90. Image processor 54 executes these instructions using predetermined parameters retrieved from a RAM and the images from the frame buffers. The results of the inspection job are directed into a mailbox memory means for use by the I/O processor 56.

The I/O processor of means 56 keeps track of the position of containers and the test results and provides pass and fail outputs based on the test results. The I/O processor tracks parts and their respective test results by acting as a variable size serial shift register. Inspection results are transferred into the register and are clocked through the register. The timing of this clock is controlled by the pulses sent by an internal rotary encoder coupled to the material handling means 80. The length of the shift register determines the distance between the part-present input and the reject output. This is set through software calibration in program mode. In addition, the I/O processor also instructs the vision computer 50 when to fire the strobe lighting system 42 to acquire images through the camera 30. To acquire a precise image of the bottom surface of the container, the strobe light source 40 is fired when the container 24 is centered in the field of view of camera 30, and this calibration is also set in program mode of the system 20.

The system 20 of this invention can be integrated onto a glass manufacturing line to allow 100 percent inspection of the glass container bottoms. The sophistication of system 20 enables it to effectively ignore the baffle mark appearing in the bottom surface of the container. As described above, the baffle mark is a mold marking caused by the two-step glass manufacturing process well known to those in the glass manufacturing industry. The baffle mark is generally circular in shape and may appear in different locations on the bottom of the container. The baffle mark is usually acceptable by the glass manufacturer and ultimate user but presents difficulties in the inspection of glassware. The baffle mark can produce a high-contrast optical signal which is often confused with the signal from an actual defect in the glass of the bottom surface thereby, resulting in the rejection of an acceptable container.

The system 20 of this invention searches for a baffle mark in the acquired image of the bottom surface and, upon finding a baffle mark, erases it from the image memory prior to the initiation of the inspection sequence. The system and method of this invention does not affect (not erase) the significant defects in the search area, even in the event such defects are located directly on the baffle mark itself. This invention allows high sensitivity settings for defect detection while maintaining a low false reject rate due to the baffle mark.

As noted, the vision engine means 50 of this invention, in a preferred embodiment, processes the acquired image of the bottom surface 22 of the container utilizing multiple processors. Preferably, six processors are used: the vision processor 54, an accelerator board, a sync board, two frame buffers, and the I/O processor board of CPU 56. The vision processor board of vision processor 54 governs the operation of the vision system 20 and generates the system sync signals, changes the analog image to digital information, passes the digital information through the look-up table, stores and retrieves the digital image in one of the frame buffer boards, changes digital information to an analog image, carries an operating system PROM and a user RAM, runs the inspections on portions of images, and sends inspection results to the I/O processor. The vision processor 54 is preferably controlled by a microprocessor coupled to the accelerator board to operate the system 20 at 25 MHz. A suitable microprocessor to control the vision processor board is manufactured by Motorola as model No. 68020.

The accelerator processor board, which carries the microprocessor governing the vision processor board and its peripheral chips, is primarily responsible for increasing the operational and manufacturing speed of system 20. More particularly, the accelerator increases the operational speed of system 20 from 12.5 MHz to 15 MHz enabling system 20 to process up to 350 parts per minute.

The sync board (not shown) receives the vertical and horizontal sync drive signals from the vision processor 54 and amplifies and splits them into signals for the monitor and for each camera (if more than one is used). A ribbon cable carries the sync signals to the camera distribution board where they are distributed to the cameras. The same signals are distributed, via other ribbon cables, throughout the system 20 for system synchronization.

A preferred embodiment of system 20 includes two frame buffer boards as part of means 52, one of which stores the digitized image from the camera and the other of which stores color graphic menus and image overlays.

The CPU 56 controls the inputs and outputs to and from system 20 and is coupled to a second microprocessor 58 which controls the functions of CPU 56. This arrangement allows the I/O processor board to run simultaneously with but independently from the vision processor 54. A suitable microprocessor 58 for controlling the CPU 56 is manufactured by Motorola as Model No. 68000.

User interface 90 of system 20 allows the operator to communicate with the system 20 and generally consists of the monitor 92, keyboard 94, and a LED remote I/O display (not shown). The monitor 92 displays the video images of the bottom surfaces being inspected as well as various prompts and instructions directed to the operator.

The machine interface means utilized by system 20 preferably is part of CPU 56 and includes a plurality of parallel I/O channels, a plurality of strobe I/O channels for the strobe lighting system 42, and at least one serial communication port. Part-present inputs and test results are communicated through optically isolated parallel I/O channels while more complex information, such as coordinates for robotic guidance or statistical information, is communicated through serial ports. The strobe I/O board is connected directly to the vision processor 54 which then controls the stop SCCD and fire strobe signals through light source 40 and monitors the part-present signals generated by position sensor 84.

The camera distribution board, as mentioned above, is a series of connectors. Horizontal and vertical sync signals from the sync board are distributed to the camera(s) through these connectors. Some of these connectors receive the RS170 video signals from the camera(s) and pass the signals on to the vision processor board.

There are generally two available methods for synchronizing the camera 30 with the lighting system 42 to ensure that an accurate image is acquired by the system 20 for processing. Either option may be selected when, as will be discussed in further detail below, the operator creates a task to be performed by the system 20. These options are: "strobe" and "frame reset". "Strobe" fires the illumination source 40 and acquires an image of the bottom surface 22 at the next vertical retrace. "Frame reset" fires the illumination source 40 and acquires an image immediately. The difference between using "frame reset" or "strobe" is determining when it is desired for illumination source 40 to flash. If strobe is selected, illumination source 40 is fired on the next vertical retrace of the camera after receiving a part-present signal from sensor 84. This is commonly referred to as being "video synchronous". If "frame reset" is selected, illumination source 40 is fired immediately upon receipt of the part-present signal from sensor 84. Generally speaking, illumination source 40 must be triggered to provide a light pulse when the container 24 is located in the proper viewing area of camera 30 to conduct testing effectively.

The system 20 of this invention is operable in two modes: a training or program mode and an inspection or run mode. The training or program mode is used to train or educate the system 20 on a particular glassware product, e.g., the glass container or jar 24. The inspection or run mode is used for the actual testing of the product on-line.

Before any inspection sequences may be initiated, the system 20 is first operated in the training mode to provide the system 20 with criteria for acceptable glass containers. In the training mode, an acceptable container (a container that has previously been determined as acceptable by whatever means) is placed in the optical path or field of view of the camera 30 to permit the system 20 to acquire the image of the bottom surface 22 of the acceptable container. The operator then defines a set of acceptable parameters for this image, including pass/fail criteria. The good or acceptable container criteria are then stored in the vision computer means 50.

For each inspection of the bottom surface of a container, any baffle mark present in the bottom surface must be removed from the image memory prior to analysis of the image for defects in the bottom surface. An "edge" is part of an image of the bottom surface 22 of the container characterized by rapid changes in intensity values of the pixels at the borderline between distinct regions of the image. Edges are recognized by the system 20 by the change in the gray shades value of the pixels. As noted above, the brightness of each pixel in the particular image has previously been measured and assigned a gray shade number between one and 256, which gray shade value for each pixel of the image has been stored in memory, the brighter the image value, the higher the number. The presence and location of detected "edges" (i.e., distinct transitions in the grade shade number of adjacent pixels) are used to locate and identify the center of an image, locate and identify any baffle mark present in the image and identify defects.

In setting up the system 20, the operator determines annular areas of the image in which baffle marks of acceptable containers are expected. These inspection areas, or "donuts", let the operator divide the image of the bottom surface so the system analyzes only that portion of the image in which a baffle mark is expected. FIGS. 5A and 5B illustrate an image 23 of a bottom surface 22 of the container 24 showing the baffle mark 25 present in the image. Frequently, only a portion of baffle mark 25 is present in the image as a result of its illumination, as shown in FIGS. 5A and B. The donut 26 is defined by two concentric circles 26a and 26b that the operator positions during the setup of the system. The size and position of the circles 26a and 26b are variable and defined by the operator through interface means 90. During the inspection of glassware, the inspection area between the two concentric circles 26a and 26b is examined at a plurality of equally spaced locations to identify the edges, if any, at those locations. The image processor then analyzes the locations of any edges detected in sets of three adjacent locations, determines the center location and radius of any circle containing the three adjacent locations, correlates the center and radius data to determine if data reliably identifies a baffle mark, and stores and uses the center and radius data to effectively ignore the edge signals of any baffle mark in analyzing the image for defects. A similar process can be used to ignore the signals at the boundaries of the glassware image, referred to as "the heel mark." For example, edges that are part of a baffle mark 25 can be removed from the image memory, and the number of remaining edge points detected can then be compared to a predetermined allowable maximum number of edge points that define acceptable glassware. As indicated above, system 20 can be adapted to distinguish between the heel mark 27, which will be interpreted as an edge, and other edges which may be interpreted as unacceptable defects.

To set up the system 20 to distinguish heel marks, concentric circles defining a filter donut, substantially identical to filter donut 26 shown in FIG. 5B, are arranged so that the heel mark 27 lies between the boundaries of the donut. As with the baffle mark filter donut 26, the edge detection inspection circles may be moved, enlarged or contracted by the operator through user interface means 90. The inside inspection circle may not be made larger than the outside inspection circle, but the inside inspection circle may be made so small that it effectively disappears. If the inside inspection circle is made to effectively disappear, all of the area within the large inspection circle will be analyzed by the system 20. If the inside inspection circle 26b is expanded to define a donut-shaped area, the area between the two circles 26a and 26b will be analyzed by the system 20. When the system 20 identifies the heel mark during a particular inspection sequence, it can remove the heel mark from the image memory to avoid confusing the heel mark signals with signals indicating unacceptable defects in the image 23.

During the system training mode (i.e., the system set up), the operator sets up a filter donut 26 for the baffle find process and an operating program stored in the vision computer 50 then determines the boundary parameters of the filter donut 26. In the baffle erase process, however, the operating program of the system 20 defines its own filter donut 26. To the operator, these processes appear as one because after the operator defines the filter donut 26, the baffle find parameters and the baffle erase donut are defined instantly by the operating program.

The baffle find filter donut 26 determined by the operator may be defined using expand and contract control keys provided by the user interface 90. When the donut 26 surrounds the entire baffle mark 25, with sufficient room on each side of the baffle mark for variations in baffle locations among the various containers, the operator then instructs the system 20 to enter the filter donut 26, thereby training the system 20 on locating the baffle mark 25. Parameter values for finding the baffle mark 25 are automatically chosen by the operating program of the system 20. The operator may change these parameters, if desired, through interface means 90.

The next step in the erase baffle sequence is to set up the parameters for the baffle erase job. This job may entirely remove the baffle mark 25 from the image 23 or merely soften it by changing the darker gray values of the baffle mark 25 to correspond with the gray values of the pixels surrounding the baffle mark 25. The operator may also choose how much of the baffle mark 25 to remove, if desired. In a preferred embodiment of the system 20, the operating program of the vision computer 50 automatically sets up the test parameters for erasing the baffle. The operating program calculates the best possible baffle erase parameter value. Alternatively, the operator may choose to determine the parameters himself or modify the automatically chosen values. After the system 20 has found (registered its location) and determined the size of the baffle mark 25, system 20 removes (paints out) from the memory information corresponding to the baffle characteristics, leaving only image information distinguishable from the baffle mark 25. The image 23 has now been filtered (baffle mark removed) and is now ready for inspection.

(System 20 can work effectively with only part of the baffle mark 25 visible as shown in FIGS. 5A and B.)

In the training mode, the edge detection filter donuts are also defined by the operator. The operator may define as many edge detection circles or donuts as desired. However, the larger the area within the donut boundary that is searched, the longer each inspection takes.

An inherent problem in any machine vision system is locating the position of a part in the field of view of the image acquiring means. The system 20 of this invention is capable of inspecting containers whose location varies slightly in the field of view of the camera 30. As a part of its operating program, system 20 is provided with software that locates the edges of the bottom surface of the container and places the inspection circles relative to these edges. That is, the system 20 examines the image of the bottom surface 22, determines the boundaries of the bottom surface and positions inspection circles consistently within the image even if its location varies in the field of view.

Figure 5C:
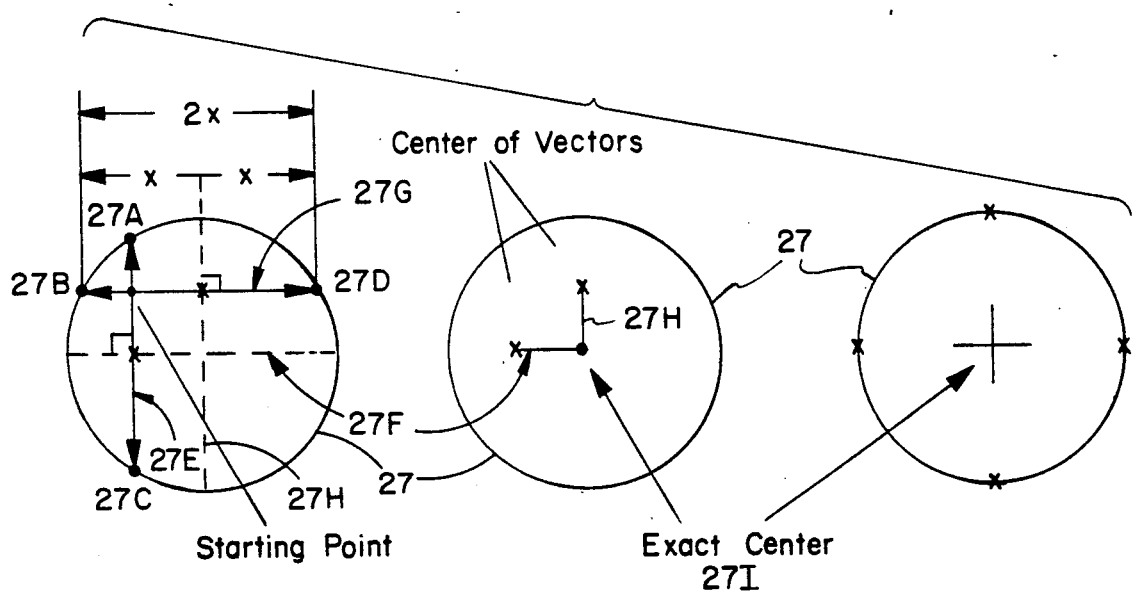
FIG. 5C is a series of plan views of an image of the bottom surface of a container being inspected by the invention to illustrate the manner by which the invention locates the center of the image.

In accommodating variable locations of the part in the camera's field of view, the exact center of the circular image 23 is located. As shown in FIG. 5C, the system initially detects an edge corresponding to the heel mark 27. The system 20 then identifies at four random sites 27a, b, c, d along the edge defining the heel mark 27. System 20 then draws a first vertical line 27e from two of the sites 27a and 27c. System 20 then draws a second line 27f bisecting first line 27e at a perpendicular angle. Thereafter, system 20 draws a third line 27g from a third site 27b to a fourth site 27d. System 20 then draws a fourth line 27h bisecting the third line 27g. Second line 27f and fourth line 27h intersect at a point 27i, which defines the center of the image of the bottom surface 22 of the container. The system 20 can then position the donut-shaped inspection areas for the baffle mark and heel mark substantially concentric with the center 27i.

Figure 6:
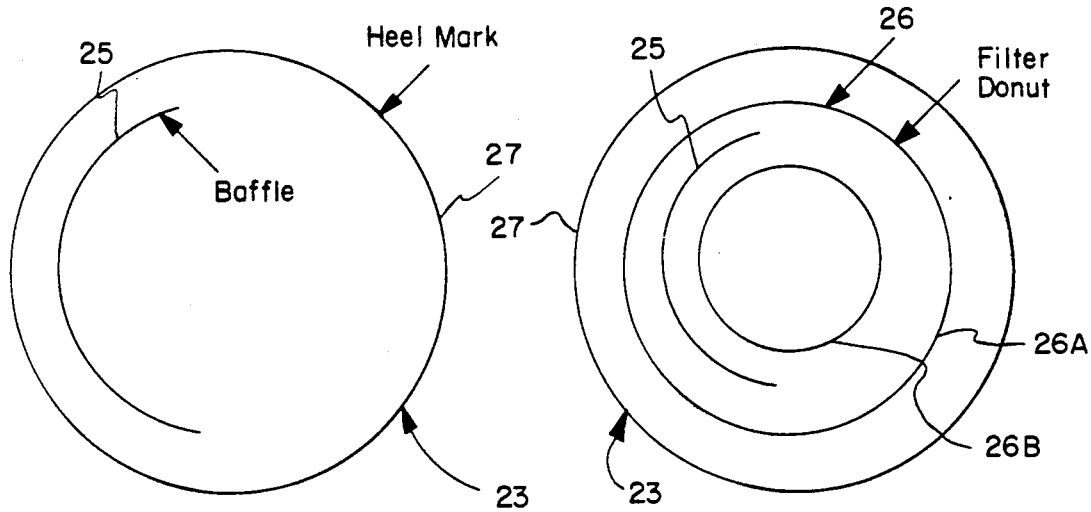
FIG. 6 is a plan view of an image of the bottom surface of a container being inspected by the invention to illustrate the manner by which the invention processes the image utilizing a multiple circular edge detection method to detect defects or otherwise unacceptable marks in the bottom surface.
Figure 6:
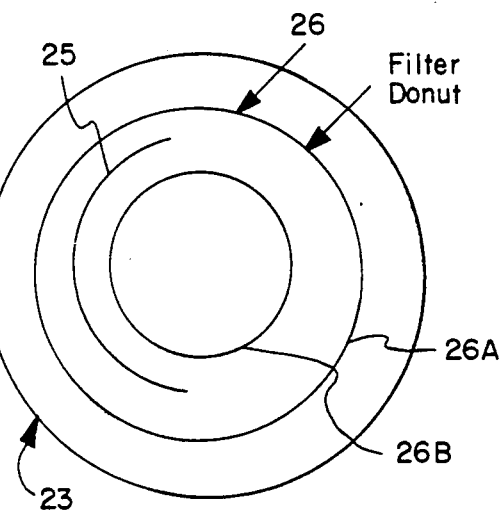
Figure 6:
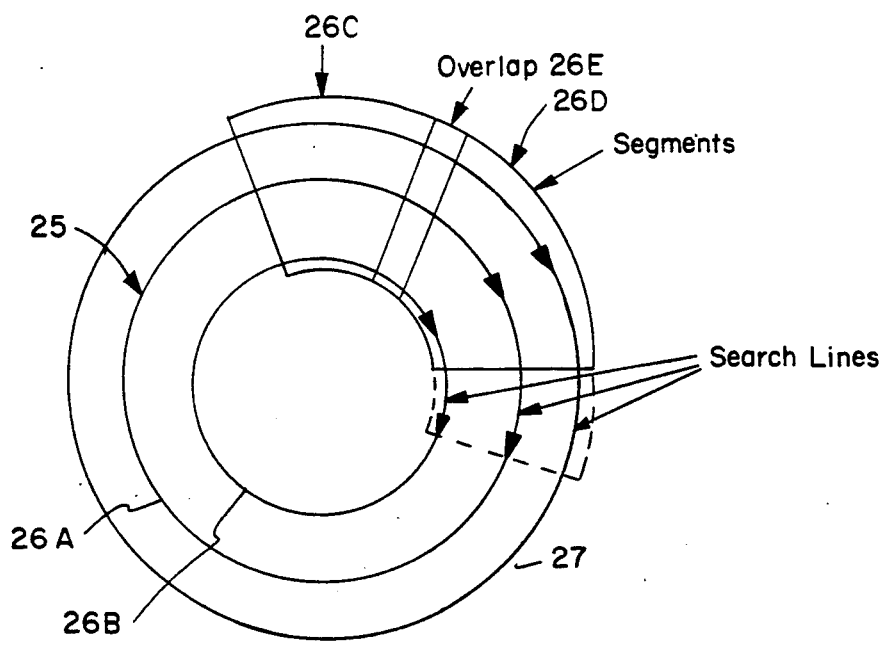

In searching for the edges during the training mode, the system 20 can search for edges vertically and horizontally in an "X/Y scan" or in a circular fashion about the image in a "circular scan". The circular scan technique is shown in FIG. 6 where the inspection donut 26 is divided into segments 26c, 26d, and so on in a similar fashion. The inspection donut 26 may be divided into any convenient number of segments.

If the X/Y scan is selected, also referred to as the "linear edge detection" method, the entire donut as shown in FIG. 7B, or the area inside of the outer inspection circle 26a as shown in FIG. 7A, is searched horizontally and vertically. The linear edge detection method is useful in finding defects if the defects are located concentric with the image 23 or near the edges of the image.

The parameters to distinguish defects include a gradient, a delta, and baffle thickness. With respect to the multiple circular edge detection method, the number of segments and the minimum/maximum edge points that may be found must also be defined.

The gradient is a minimum difference between gray shade values of pixels being compared that determines an edge. This value is calculated from the gray shade values of the pixels under consideration. The gray shade values of two pixels (separated by delta, which is discussed below) are compared and if the difference between the shades is greater than or equal to the gradient, an edge is defined. For example, if the delta is preset at two, at the beginning of the system's search for an edge, the system 20 compares the shade (light intensity) of the first pixel in the circle to the shade of the third pixel, the shade of the second pixel to the shade of the fourth pixel, then the third to the fifth, and so on in a like fashion around the circle. If the gradient is preset to 15, an L edge is found when there are 15 gray shades of difference between the two pixels being compared. The gradient is automatically chosen by the operating program of the system 20, or the gradient may be manually set if desired. For example, if the system 20 is overlooking an edge that is of interest, the gradient may be lowered to detect the edge. Conversely, if the system 20 is detecting variations near the baffle mark or the flaw edges that are too small, the gradient may be increased to lessen the sensitivity of the system 20.

Delta is the distance between the pixels whose shades are being compared when the system 20 is looking for an edge. Preferably, the delta is adjustable between one and five. For example, if the delta is set at three, the first pixel is compared to the fourth pixel, the second to the fifth, the third to the sixth, and so on in a like fashion. The delta is useful in detecting hard-to-define edges. A delta of only one or two detects sharp edges, whereas a higher delta is better for fuzzy or unclear edges. The system 20 of this invention is, preferably, programmed to automatically choose a delta of three which is considered best for most applications.

"Baffle thickness" is the largest width of a mark which qualifies as part of the baffle mark 25. The baffle thickness is preferably adjustable between one and 100. If, for example, a baffle thickness is set at ten, the baffle may be no more than ten pixels in width to be considered only the baffle and not be identified as a defect. Baffle thickness is used to distinguish between the baffle mark and the defects located "on" the baffle mark. As shown in FIG. 8, the system 20 of this invention can distinguish between the baffle mark 25 and a type A defect that is not located on the baffle mark, and between the baffle mark and a type B defect falling on a baffle mark 25 which has a pixel width significantly greater than the predetermined baffle thickness. However, the system 20 of this invention cannot distinguish between the baffle mark 25 and type C defect falling on the baffle mark and having a pixel width smaller than or about the same size as the predetermined baffle thickness.

A further parameter that is determined prior to the initiation sequence is the "scan increment". The scan increment is the number of lines skipped between lines scanned within the search donut or inspection circles. This value is adjustable between one and 20 and the smaller the scan increment, the more accurate the inspection, yet, the slower the inspection sequence.

A further parameter that may be defined is the "edge thickness". The edge thickness is similar in concept to the baffle thickness. Edge thickness is the number of consecutive pixels that must have the prescribed gradient difference to define an edge. For example, if the edge thickness is preset at five, five consecutive pixels must have the prescribed gradient difference to define an edge. The edge thickness is adjustable from one to 100.

Another parameter to be determined is the number of "good part minimum edge points" which sets an acceptable range by defining the minimum number of edge points that the system 20 can find either in the whole donut or in each segment of the inspection donut. If more than the predetermined minimum number of edges is found, the part passes. Related to this parameter is another parameter that must be determined which is the "good part maximum edge points" which sets an acceptable range by defining a maximum number of edge points the system 20 can find either in the whole donut or in each segment of the donut. If less than the predetermined maximum number of edges is found, the part passes.

An optional but useful feature that may be implemented in the system 20 is to include means for monitoring reject limits of the system 20. There are normally two such reject limits, the maximum reject rate and the maximum consecutive rejects. This data enables the operator to detect a flaw in the manufacturing process with a minimum amount of product being wasted. For example, if the maximum number of consecutive rejects is set at five, and five parts in a row fail for any reason, an output is generated which is usually connected to a warning beacon or alert unit of some type. The maximum reject rate is the percentage of parts rejected. If, for example, the maximum reject rate is preset at five percent, and after 100 parts have been tested over five percent of the parts have been rejected, another similar alerting output is turned on.

As noted above, the system 20 of this invention is calibrated so that the strobe flash may be coordinated with the center of the jar 24. These calibration functions are automatically determined and carried out by the operating program of the system 20. More particularly, the operating program automatically calibrates the "part width" which measures the width of the container 24 in order to fire the strobe illumination source 40 when the middle or center 27i of the bottom surface of the container is directly beneath the camera 30. In addition, the operating program calibrates the "reject delay" which determines the distance or time the container travels between the inspection point and the rejection station. Each calibration's system employs a combination of encoders, photosensors and reject pulses.

Once the system 20 is set up and operable to initiate the inspection sequence on-line, the system 20 may then be instructed via the user interface 90 to begin operating in the run or inspection mode.

In partial summary, while in the inspection mode and during each inspection sequence, the system 20 acquires the image of the bottom surface 22 of each container 24, identifies the baffle mark 25, if any, within the image 22, erases or removes the baffle mark from the image memory, inspects the remaining image by analyzing circular or donut-shaped inspection areas of the image and processes any marks or defects discovered in the image by comparing them to the predetermined acceptable criteria to determine whether the container is acceptable, and generates the rejection signal if the container is unacceptable to effect the removal of the container by reject mechanism 88.

Shown in FIGS. 9-12 are flowcharts illustrating a method of operation of this invention and a system operating program for the vision computer 50 according to this invention. It should be understood that prior to the occurrence of any actions described hereinafter, the training of the system 20 has been completed and all necessary parameters and criteria have been determined and entered into the system 20.

Figure 10:
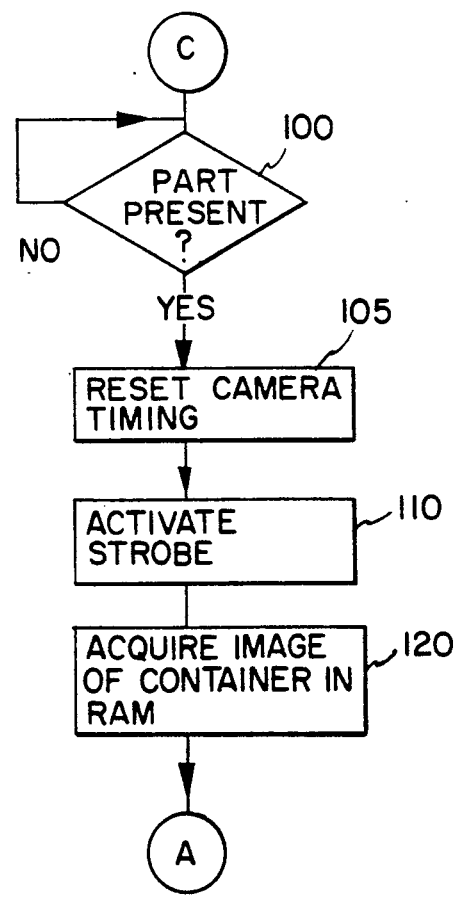
Figure 11A:
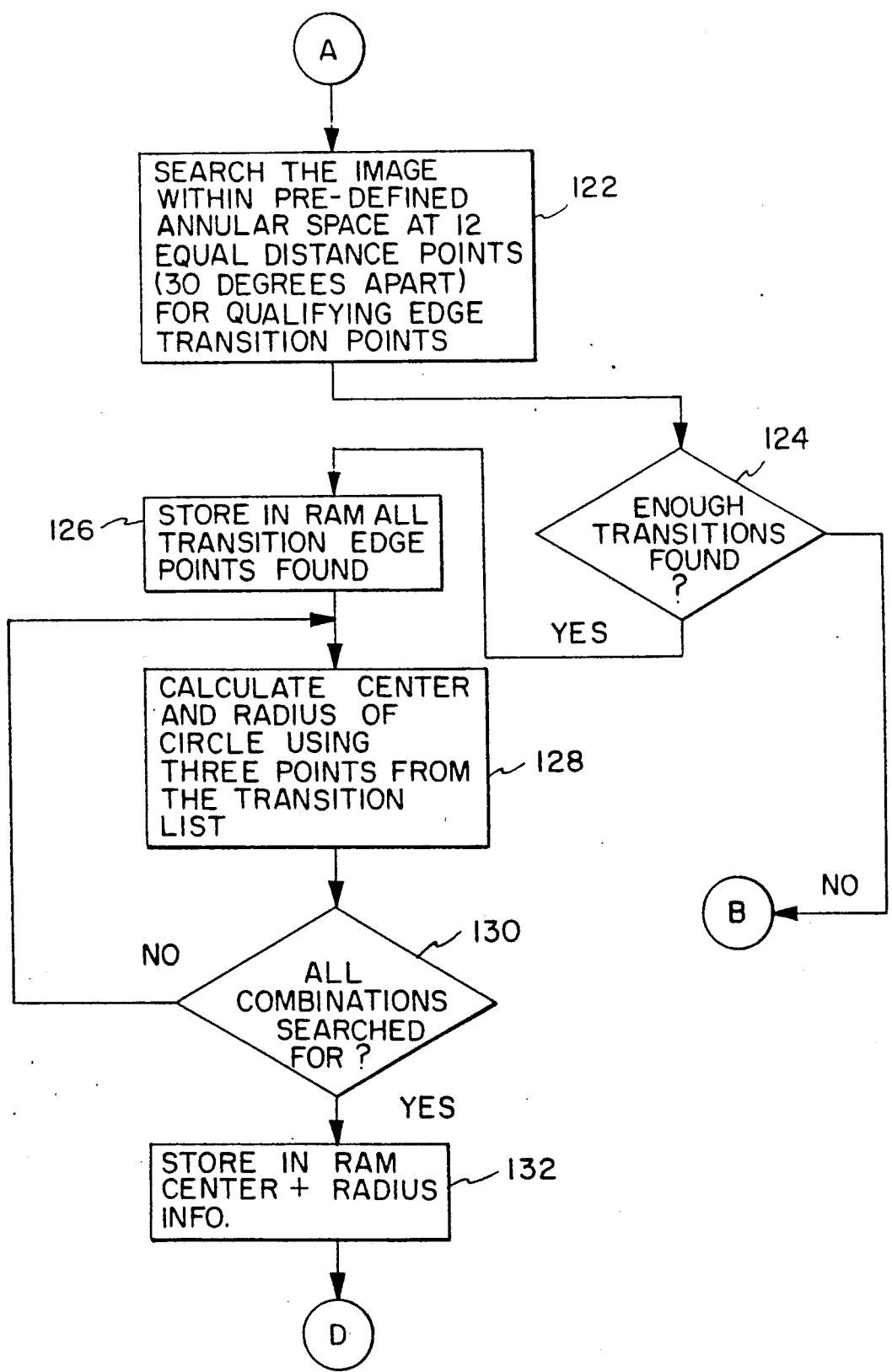
Figure 12A:
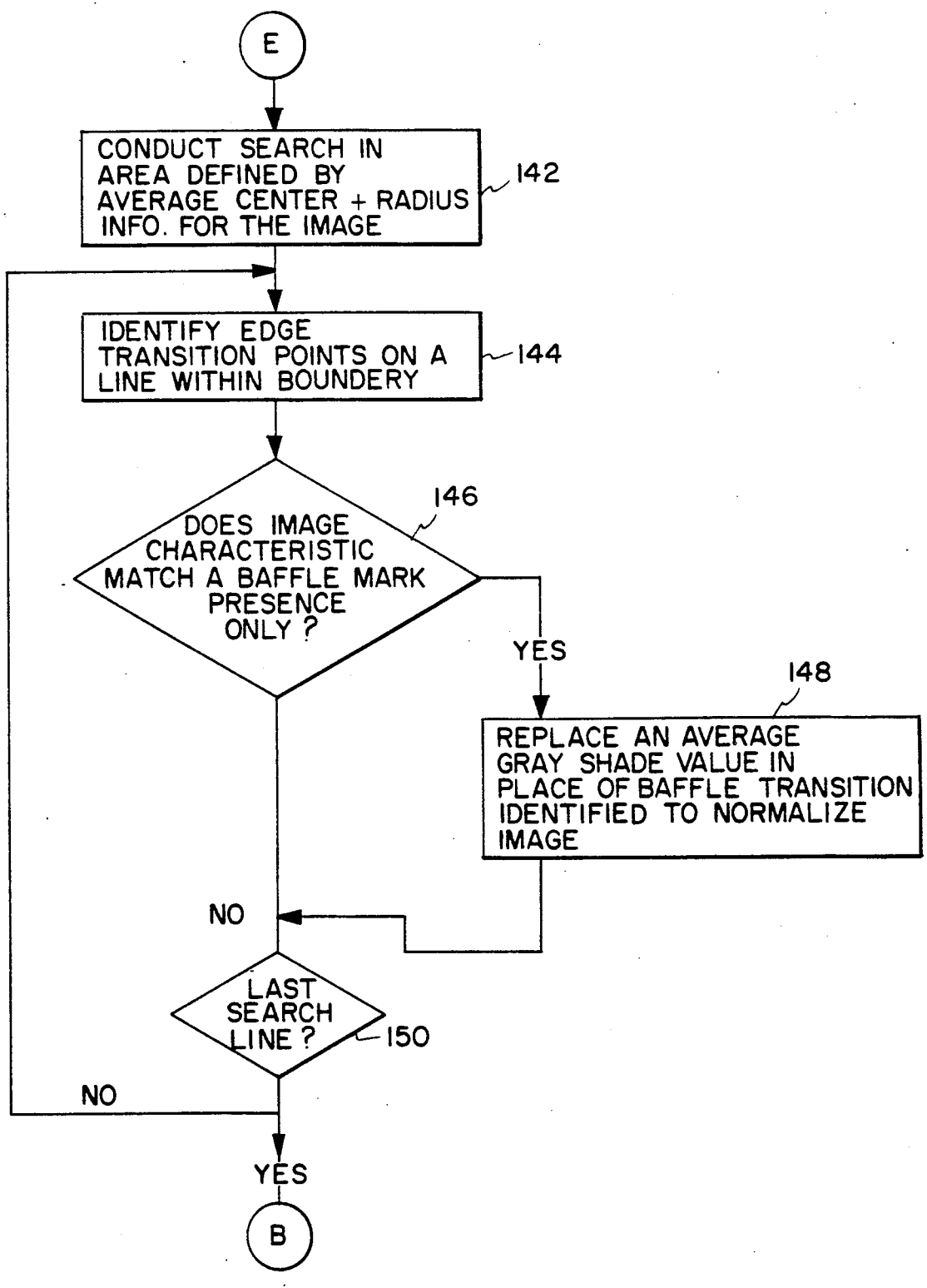
Figure 11B:
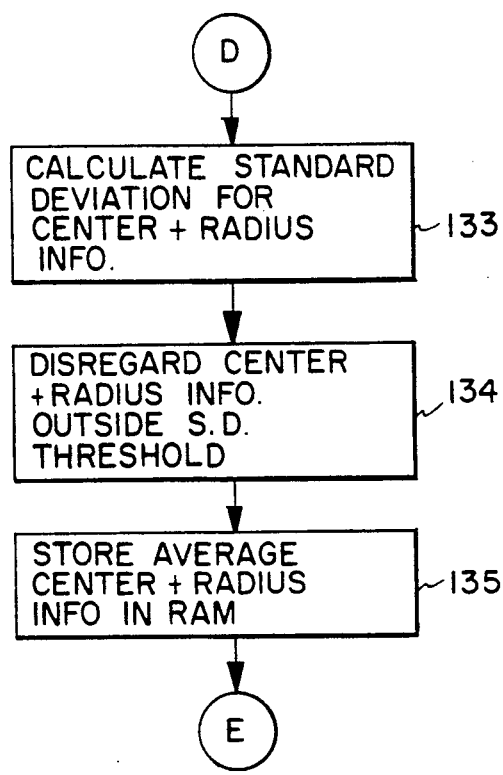
Figure 12B:
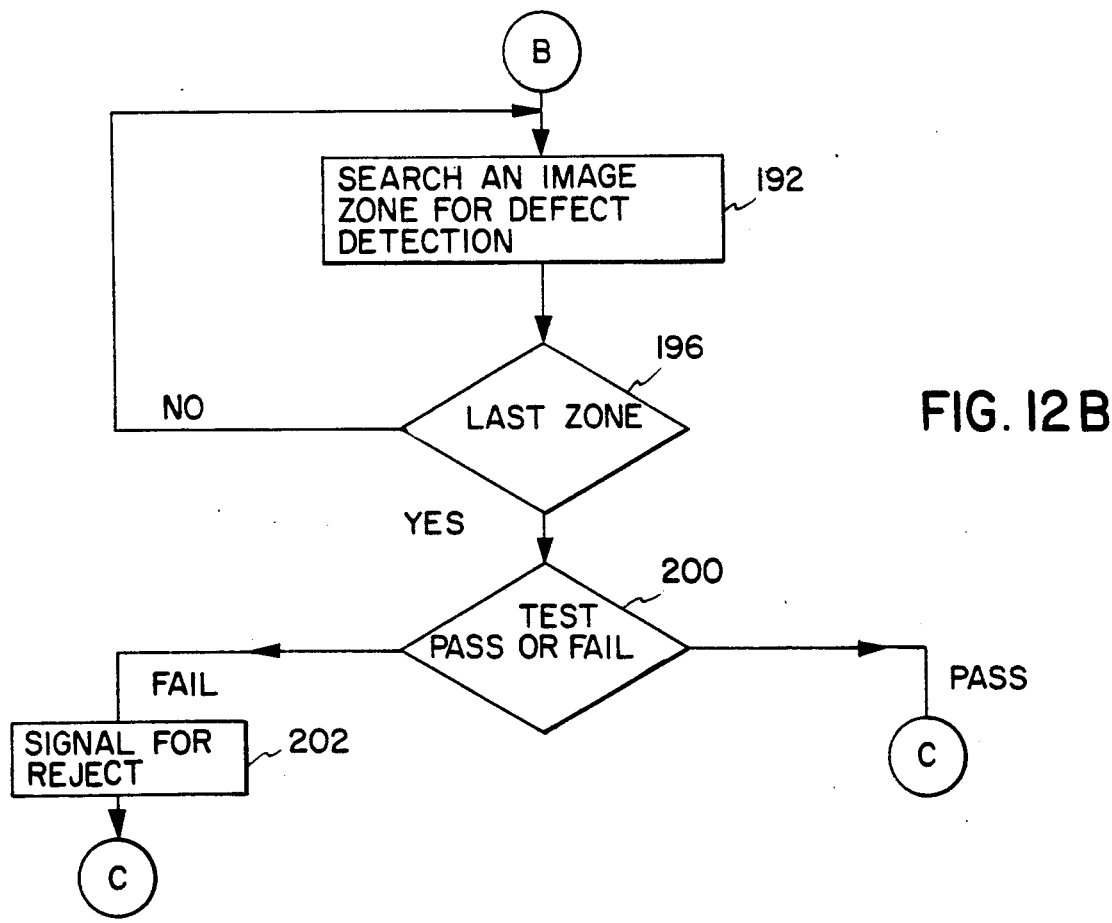

Each of the FIGS. 10-12 begin and end in an encircled letter to indicate the relation of the flowcharts presented in FIGS. 10-12. For example, the flowchart of FIG. 10 is ended by an encircled A while the beginning of the flowchart of FIG. 11A is indicated as well by an encircled A. This indicates that the progression of the flowcharts proceeds from box 120 to box 122 of FIG. 11A. Similarly, the encircled D of FIG. 11A directs the reader to the beginning of FIG. 11B while the encircled B of the FIG. 11A directs the reader to the beginning of FIG. 12B.

Figure 9:
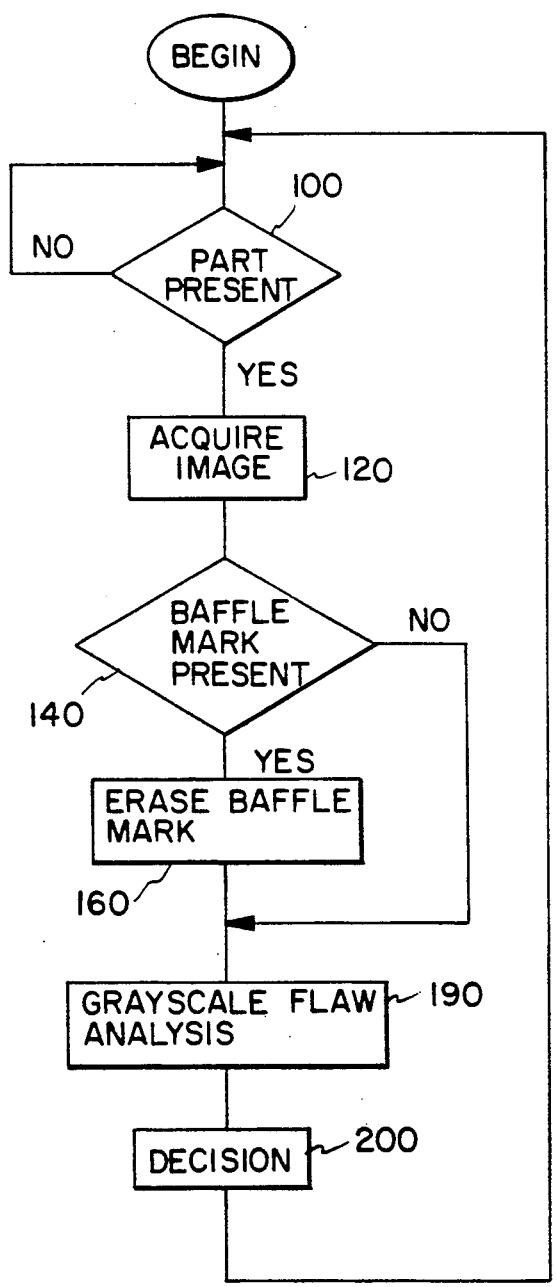
FIGS. 9, 10, 11A, 11B, 12A, and 12B are flowcharts of one preferred method of this invention.

As shown in FIG. 9, system 20 of this invention initiates an inspection sequence of the bottom surface 22 of a container 24 when a part-present signal is generated by sensor 84 as shown in diamond 100. The vision computer 50 then instructs the image acquiring means 30 to acquire an image of the bottom surface of the container, as shown in box 120, after which the vision computer 50 determines whether a baffle mark is present in the bottom surface of the container, as shown in diamond 140. If a baffle mark is not present in the image, the vision computer analyzes and processes the image to determine its pass/fail status, as shown in boxes 190 and 200. If system 20 does identify a baffle mark present in the image of the bottom surface, the system erases the baffle mark 25 from the image as shown in box 160 and thereafter proceeds to process and analyze the now filtered image and to determine its acceptability, as shown in boxes 190 and 200.

Shown in FIGS. 10-12 are more detailed flowcharts illustrating the method of operation of this invention and of the system operating program for the vision computer 50 employed by this invention. As just described and as shown in FIG. 10, system 20 initiates an inspection sequence upon being notified by sensor 84 that a container is present at the inspection zone beneath the camera 30, as shown in diamond 100. Upon receipt of the part-present signal from the sensor 84, the vision computer 50 resets the timing of the camera 30 and synchronizes the strobe illumination source 40, as shown in boxes 105 and 110. Upon the synchronization of the camera 30 and the strobe light source 40, an image of the bottom surface 22 of the container is acquired in digital signal format, as shown in box 120. The acquired image is then stored in RAM pending subsequent processing and analysis.

Shown in FIG. 11A is the baffle mark registration method carried out by the vision computer 50 utilized by this invention. As shown in box 122, the system 20 initially searches the image within a predefined annular boundary (the filter donut 26 shown in FIG. 5B) at 12 points spaced at equal distances (30° apart) about the annular boundary for identifying transition points. If an insufficient number of transition points are found, the system 20 continues its search and inspection of the image zone for any further defects, as shown in diamond 124. This particular scenario where insufficient transition points are found will be discussed further in relation to the flowchart presented in FIG. 12B.

If a sufficient amount of transition points are found by the system 20, the system stores this data in the RAM, as shown in box 126, and then proceeds to attempt to locate the precise position of the baffle mark by calculating the center and the radius of the transition points detected within the filter donut 26, by fitting circles to sets of, preferably, three adjacent points from the transition list, as shown in box 128, and determining a single circle with a minimum baffle thickness that fits the transition points. When a combination of the transition points detected in the filter donut 26 has been analyzed and a baffle mark center and radius have been calculated from such combinations, the system 20 then stores this data in RAM as shown in diamond 130 and box 132. If all the programmed combinations of the transition points have not been searched and the center and radius of same calculated, the system 20 continues its calculations until all the combinations have searched for and calculated.

Referring now to FIG. 11B, once all the programmed combinations of the position points discovered in the filter donut have been searched for and their centers and radii calculated and stored in RAM, the system 20 then proceeds to calculate the standard deviation for the centers and radii data, as shown in box 133, disregarding any center and radius information outside the standard deviation threshold, as shown in boxes 134 and 135. At this point, the location and size of the baffle mark on the container has now been identified by the system 20 and has been stored for use during the inspection sequences. This information will be used during the inspection of the container to filter out the baffle mark from the image memory.

Referring now to FIG. 12A, the system has at this time stored the average center and radius information in the RAM representing the location and size of the baffle mark in the bottom surface 22 of the container 24 being inspected, as shown in FIG. 11B, and now proceeds to search or inspect the image of the bottom surface in the inspection circle portions defined by the average center and radius information as shown in box 142. The vision computer 50 then identifies edge transition points within the annular boundary and determines whether the characteristics of these identified edges correspond with the baffle mark data previously determined and stored in the RAM, as shown in box 144 and diamond 146. If the image characteristics of the identified edge transition points do correspond with the baffle mark data, the vision computer 50 substitutes in place of the baffle transition points an average gray shade value to normalize that portion of the image, as shown in box 148. The average gray shade value is provided by the operating program of the vision computer 50. This eliminates the contrast between the baffle mark 25 and the surrounding pixels to avoid generating a false rejection signal due to the baffle mark. If not filtered, the baffle mark image would fall outside of the acceptable gradient and delta criteria and generate a rejection signal for an acceptable container.

In the event the image characteristics of the edge transition points identified in box 144 do not correspond with the baffle mark characteristics on a search line, the vision computer 50 stores the transition points for defect analysis and then determines whether it has inspected all of the search lines, as shown in diamond 150, and if not, the computer proceeds to the next search line to identify edge transition points and continues until all search lines within the annular boundary of the inspection circle have been analyzed, as shown in box 144. If the vision computer determines that it has searched all the search lines falling within the annular boundary of the inspection circle, it then proceeds to search the entire image of the bottom surface 22 of the container, utilizing the multiple circular edge detection technique or the linear edge detection technique (illustrated in FIGS. 6 and 7A and B, respectively) as shown in box 192 of FIG. 12B. The vision computer 50 continues its inspection of the image searching for defects in the glass and continues to do so until it determines that it has searched all the search zones into which the image has been sectioned by the operating program stored in the vision computer 50, as shown in diamond 196. If not, vision computer 50 continues its search into another image zone searching for defects as shown in box 192.

If the vision computer 50 determines it has searched every image zone, it then proceeds to conduct the gray scale flaw analysis test and determines the pass/fail status of the container 24 being inspected as shown in diamond 200. If the sensed data from the image of the container being inspected falls within the predetermined acceptable parameters, the vision computer 50 identifies the container as acceptable and terminates the inspection sequence for that container and awaits the next part-present signal from sensor 84, to initiate the next inspection sequence, as shown in diamond 100 of FIG. 10. If the vision computer 50 determines that the sensed data of the image being inspected falls outside of the acceptable predetermined parameters, the vision computer 50 identifies that container as unacceptable and tracks the unacceptable container, and when the container reaches the rejection zone, the vision computer 50 generates a rejection signal, as shown in box 202, directed to the reject mechanism 88 (FIG. 2) to effect the removal of the unacceptable container from the manufacturing line.

This invention thus includes a machine vision inspection system that processes and inspects images of the bottom surface of glass containers by a television camera, identifies the baffle mark formed in the bottom surface and filters out this baffle mark from the image memory prior to inspecting the image for defects, thereby avoiding false rejection signals. The vision computer is programmable to engage in multi-tasking and is programmable through a user interface to allow an operator to create a set of performance features or jobs unique to the desired task(s). These features are then automatically stored in the vision computer's memory means. Moreover, the sensitivity of the inspection system presented by this invention may be determined as desired for particular applications.

The system and method of this invention make sophisticated inspection of glass containers possible with much better repeatability than conventional systems or methods. Further, this invention is also capable of inspecting non-round glass containers and can easily accommodate change-over to many jobs. The features and parameters of the vision computer 50 are adjustable to enable the system to accommodate many system variables, and allows the system and method of this invention to operate quickly and accurately over prolonged periods of operation. The vision computer of this invention utilizes multiple processors to perform desired tasks. The image processing analysis is controlled by an operating program stored in the vision computer. The system and method of this invention thus enjoys enhanced flexibility and high inspection speeds.

Although the system and method of the present invention have been described with preferred embodiments, those skilled in the art will understand that modifications and variations may be made, without departing from the scope of this invention as set forth in the following claims. Such modifications and variations are considered to be within the purview and scope of the appended claims.

What is claimed is:

1. A method of inspecting a substantially transparent container being transported by a conveyor means, said container having a baffle mark formed in the bottom surface thereof, said method comprising the steps of:
   illuminating the bottom surface of said container;
   acquiring an image of the bottom surface of the container;
   identifying the baffle mark present in the image;
   analyzing the resulting image while ignoring the baffle mark to identify any remaining marks in the bottom surface of the container;
   determining whether any of said remaining marks are acceptable; and
   removing the container from the conveyor means if any of said remaining marks are unacceptable.

2. The method as in claim 1 wherein said acquiring step includes storing the image in an image memory means, and wherein said identifying and analyzing steps include locating the baffle mark within the image and erasing the baffle mark from the image memory means.

3. The method as in claim 1 wherein said illuminating step is carried out by a difficult light source, and wherein said acquiring step is carried out by a camera.

4. The method as in claim 1 further comprising the steps of:
   presenting the container to an inspection station and therefrom to a rejection station;
   sensing when the container is positioned at the inspection station to initiate the acquisition of the image of the bottom surface of the container;
   tracking a container that is identified as unacceptable after it exits the inspection station; and
   sensing when the unacceptable container is positioned at the rejection station to initiate the removal of the unacceptable container.

5. The method as in claim 1 wherein said identifying and analyzing steps are carried out by an operating program stored in a data processing and storage means.

6. The method as in claim 2 wherein said step of identifying the baffle mark includes registering the baffle mark present in the bottom surface of the container by determining the location and size of baffle mark and storing information corresponding to the location and size of the baffle mark in the memory means.

7. The method as in claim 6 wherein said identifying step further includes the steps of:
   characterizing the image of the bottom surface of the container by generating within the image a circular donut-shaped inspection area in which the baffle mark is expected; and
   inspecting the image within said inspection area to identify the baffle mark and erasing from the memory means information corresponding to the baffle mark;
   and wherein said analyzing step includes detecting marks in the image of the bottom surface by sensing and comparing the intensity and location of said marks with predetermined parameters to determine whether said sensed marks are acceptable, and if any sensed mark is unacceptable, generating a rejection signal to effect removal of the container.

8. The method as in claim 7 wherein said detecting step is carried out by a microprocessor operating in a multiple circular edge detection mode.

9. The method as in claim 7 wherein said detecting step is carried out by a microprocessor operating in a linear edge detection mode.

10. The method as in claim 7 wherein the bottom surface is made of glass, and wherein the location of the baffle mark and other present marks is indicated by a change in the intensity of the diffused light passing through said baffle mark and other present marks, the diffused light being blocked by said marks which appear as dark portions within the acquired image.

11. A system for inspecting a substantially transparent container having a baffle mark formed in its bottom surface, said system comprising:
   means for presenting the container to an inspection zone and therefrom to a rejection station;
   means for illuminating the bottom surface of the container at the inspection zone;
   means for generating an image corresponding to the bottom surface of the container;
   means for storing the sensed image;
   means for identifying the baffle mark present in the image; and
   means for processing the stored image of the bottom surface of the container, while ignoring the baffle mark for detecting unacceptable marks in the bottom surface of the container other than the baffle mark and for effecting the removal of unacceptable containers from the system at the rejection station.

12. The system as in claim 11 wherein said presenting means includes an optical shaft encoder for tracking the container, container handling means for transporting the container through the inspection zone and therefrom to the rejection zone, optical container position sensing means and defect removal means.

13. The system as in claim 12 wherein said container portion sensing means includes photosensitive detectors adapted to sense when the container is positioned at the inspection zone and to direct a first container present signal to the processing means to initiate the inspection sequence, and means to sense when the container is positioned at the rejection zone and to direct a second container present signal to the processing means to initiate the rejection sequence.

14. The system as in claim 12 wherein said container handling means comprises a side-grip conveyor means.

15. The system as in claim 11 wherein said illuminating means comprises a diffused strobed light source.

16. The system as in claim 15 wherein said diffused strobed light source comprises an array of solid state light emitting diodes.

17. The system as in claim 11 wherein said image sensing and generating means comprises a camera.

18. The system as in claim 17 wherein said camera comprises a solid state, metal oxide semiconductor-type, black and white television camera having asynchronous frame react capability.

19. The system as in claim 11 wherein the container bottom is positioned between the illuminating means and the image sensing means.

20. The system as in claim 11 wherein said sensing means directs the image as an analog signal to said processing means which digitizes the analog signal and stores the signal in a 320 horizontal by 240 vertical, memory matrix array, said array comprising a plurality of separate memory locations, each of which represents a single picture element.

21. The system as in claim 20 wherein said processing means is adapted to measure the brightness of each picture element, characterize each picture element by assigning each element a gray shade value dependent upon the brightness thereof, and then store the resultant characterization in a data-storage means.

22. The system as in claim 21 wherein te baffle mark is identified by:
   means for defining within the image a donut-shaped inspection area containing the baffle marks, thereby providing a confine surrounding the baffle marks;
   means for analyzing the brightness of the picture elements within the donut-shaped inspection area to determine the center and radius of the baffle mark and generating baffle mark center and radius data which it stores in the storage means; and
   means for identifying from the baffle mark center and radius data picture elements corresponding to the location of the baffle mark and changing the stored gray shade value to an average value.

23. The system as in claim 22 wherein said analyzing means comprises means for selecting sets of picture elements having abnormally dark gray values, for fitting said sets of picture elements to one or more circles, and determining from the one or more circles the presence and location of a baffle mark.

24. The system as in claim 23 further comprising user interface means coupled to the electronic data processing and storage means to allow the operator to position the donut-shaped inspection area about the baffle mark.

25. The system as in claim 24 wherein said system is programmable through the user interface means.

26. The system as in claim 21 wherein an operating program stored in the data-storage means initiates the inspection sequence by
   characterizing the image of the bottom surface by dividing the image into a plurality of circular donut-shaped inspection areas and assigning to each picture element appearing therein a gray shade value depending upon the intensity thereof;
   analyzing the resultant characterization of each inspection portion by comparing same to predetermined acceptable parameters provided by the data-storage means; and
   generating a rejection signal if the resultant characterization does not fall within the acceptable parameters.

27. The system as in claim 11 wherein said container removal means comprises a pneumatically actuated reject mechanism.

28. The system as in claim 11 wherein said system is operable in a program mode and a run mode, said mode being determined by an operating program stored in the storage means, said program mode being operable to teach the system the criteria for a predetermined acceptable container and provide the system with a set of acceptable parameters for the bottom surface of the container, said run mode being operable to effect the inspection of the containers and the identification and rejection of unacceptable containers.

29. The system as in claim 28 wherein said set of acceptable parameters includes a gradient, a delta and a baffle thickness.

30. The system as in claim 29 wherein said baffle thickness represents the largest width parameter in the sensed image which qualifies as part of the baffle, said baffle thickness being utilized to distinguish between the baffle mark and a flaw positioned at or near the baffle mark in the stored image of the bottom surface.

31. The system as in claim 22 wherein an edge is identified in the image where the difference between the brightness of two adjacent picture elements being compared is greater than or equal to a predetermined gradient, said adjacent picture elements being separated by a predetermined delta.

32. The system as in claim 31 wherein said system locates said edge and positions the donut-shaped inspection areas relatively concentric to the edge so as to properly align the image within the field of view of the image generating means.

33. The system as in claim 32 wherein said system locates the center of the bottom surface of the container by identifying at least four sites on an edge defining the circumference of the bottom surface of the container, drawing a first vertical line from a first site to a second site and thereafter drawing a second line bisecting the first line, drawing a third line from a third site to a fourth site and thereafter drawing a fourth line bisecting the third line, said point of intersection of the second and fourth lines defining the center of the image of the bottom surface, said system thereafter positioning the donut-shaped inspection areas substantially concentric with said center.

34. The system as in claim 32 wherein said system is provided a predetermined good part minimum edge value representing the minimum number of edges the system must find to accept the container, and wherein said system identifies the container as unacceptable if less than the minimum number of edges are found.

35. The system as in claim 32 wherein said system is further provided with a good part maximum edge value representing the maximum number of edges the sensing means may find in accepting the container, and wherein said system identifies the container as unacceptable if more than the maximum number of edges are found.

36. The system as in claim 11 further comprising calibration means for coordinating the illuminating means with the presenting means and for tracking an unacceptable container to a rejection zone, said illuminating means being coordinated with the presenting means so that the illuminating means illuminates the container substantially contemporaneously with the arrival of the container at the inspection zone.

37. An apparatus for inspecting the bottom surface of a glass container and determining whether the bottom surface is acceptable, said bottom surface having a baffle mark formed therein, said apparatus comprising:
   front end means for acquiring for analysis an image of the bottom surface;
   a vision engine for analyzing and processing the image, said vision engine being operable to identify marks in the image of the bottom surface and distinguish the baffle mark from other marks present in the image and to determine whether the other marks present are unacceptable;
   operator interface means for allowing an operator to communicate with the apparatus; and
   machine interface means for allowing the apparatus to communicate with remote machines.

38. The apparatus as in claim 37 wherein said front end image acquiring means comprises:
   a lighting source; and
   image sensing means.

39. The apparatus as in claim 38 wherein said lighting source comprises a diffused array of light emitting diode strobes positioned in a back-light arrangement in relation to the image sensing means.

40. The apparatus as in claim 38 wherein said image sensing means includes a solid state matrix camera adapted to view the bottom surface and generate a corresponding image in an analog signal format.

41. The apparatus as in claim 37 wherein said vision engine comprises multiple processing means provided with a plurality of input/output channels.

42. The apparatus as in claim 41 wherein said multiple processing means includes:
   vision processing means for processing the image and generating a rejection signal if the bottom surface of the container is unacceptable;
   accelerator means for increasing the operational speed of the vision engine;
   synchronization means for synchronizing the front end means with the vision engine;
   at least two frame buffer means, one of said frame buffer means being adapted to temporarily store the image of the bottom surface once acquired; and
   input/output processing means for controlling inputs and outputs of said apparatus, said input/output processing means operating substantially simultaneously with but substantially independently of the vision processing means.

43. The apparatus as in claim 42 wherein said vision processing means is controlled by a microprocessor and generates synchronization. signals to synchronize the operation of the apparatus, converts the analog image signals to digital signals, passes the digital signals through to a look up table and stores and retrieves the digital signals in the first buffer means, converts the digital signals to the analog image, stores an operating system PROM and a user RAM, initiates the inspection and directs the corresponding inspection signals to the input/output processing means,
   wherein said accelerator means increases the operational speed of the vision engine from 12.5 MHZ to 25 MHZ,
   and wherein the synchronization means receives the synchronization signals from the vision processing means, amplifies the synchronization signals and directs the amplified synchronization signals to the front end means to achieve synchronization of the apparatus.

44. A method employing a machine vision system including an electronic sensor and a computer for inspecting the bottom surface of a glass container having a baffle mark formed therein and for detecting and rejecting unacceptable containers, said glass container being transported by a conveyor means to an inspection zone and from the inspection zone to a removal zone, said electronic sensor including an image sensing means and a diffused light source, said method comprising the steps of:
   sensing when the container is positioned at the inspection zone;
   synchronizing the image sensing means and activating the light source;
   acquiring an image of the bottom surface of the container;
   searching a portion of the image within a predetermined number of annular boundaries at various points along the boundaries to identify edge transition points and determining whether a sufficient number of edge transition points have been identified,
   and if a sufficient number of edge transition points have not been identified, searching another boundary until a sufficient number of edge transition points are identified,
   and if a sufficient number of edge transition points are identified, storing in the computer all transition edge points identified and analyzing, in combinations of three, selected transition edge points to identify centers and radii of annular boundaries and storing the identified centers and radii in the computer;
   determining a standard deviation for the centers and radii, ignoring centers and radii outside of the standard deviation, and determining and storing the average center and radius in the computer, thereby determining the location and size of a baffle mark;
   searching in a second annular inspection area defined by the average center and radius for the image;
   identifying edge transition points on a plurality of lines within the annular boundary and determining if the image characteristics sensed in the second annular boundary corresponds with a baffle mark,
   and if the sensed characteristics correspond with a baffle mark, replacing the baffle transition edge points with an average gray shade value to remove the baffle mark from the image, thereby providing a normalized image ready for inspection;
   searching a plurality of annular boundaries within the resulting image for imperfections in the bottom surface until all annular boundaries have been searched and comparing identified imperfections with a predetermined set of acceptable parameters,
   and if the identified imperfections do not fall within the acceptable parameters, generating a rejection signal to remove the unacceptable container from the conveyor means.

45. The method of claim 1, wherein the image is acquired by a video camera having an array of discrete picture elements,
   wherein the bottom surface of the container is illuminated by a pulse of light of uniform intensity throughout the bottom surface of the container, and
   wherein the pulse of light is sufficiently short that the image of small discrete parts of the bottom surface are captured by the picture elements.

46. The method of claim 1 wherein said baffle mark is identified by the steps of:
   acquiring the image of the bottom surface as signals generated by an array of small picture elements and storing the image signals from the array of small picture elements as a stored array of image pixels;
   defining an annular inspection band within the stored array of image pixels within which baffle marks are expected;
   searching the stored array of image pixels within the annular inspection band to identify locations of pixels representing abnormal light intensity;
   analyzing the locations of pixels representing abnormal light intensity in sets of three adjacent locations to determine the centers and radii of circular arcs containing the locations;
   calculating from the centers and radii standard deviation data for the centers and radii and calculating from only those centers and radii within one standard deviation an average center and average radius corresponding to a baffle mark; and
   analyzing the pixels at locations spaced the average radius from the average center location to confirm the presence of a baffle mark, and if a baffle mark is present, changing the image signals at the location corresponding to the baffle mark to correspond to an average light intensity, thereby removing the baffle mark from the stored image.

47. The system of claim 12 wherein said container handling means comprises a star wheel.

* * * * *